(12) United States Patent
Wamsley et al.

(10) Patent No.: US 6,509,566 B1
(45) Date of Patent: Jan. 21, 2003

(54) OIL AND GAS EXPLORATION SYSTEM AND METHOD FOR DETECTING TRACE AMOUNTS OF HYDROCARBON GASES IN THE ATMOSPHERE

(75) Inventors: Paula R. Wamsley, Littleton, CO (US); Carl S. Weimer, Littleton, CO (US); Loren D. Nelson, Evergreen, CO (US); Martin J. O'Brien, Pine, CO (US)

(73) Assignee: Ophir Corporation, Littleton, CO (US)

( * ) Notice: Subject to any disclaimer, the term of this patent is extended or adjusted under 35 U.S.C. 154(b) by 75 days.

(21) Appl. No.: 09/602,096

(22) Filed: Jun. 22, 2000

(51) Int. Cl.⁷ .............................................. G01N 21/45
(52) U.S. Cl. ................................ 250/338.5; 250/341.8
(58) Field of Search ........................... 250/338.5, 341.8, 250/253, 372, 301, 255, 339.11, 358.1; 356/416, 437, 432, 51

(56) References Cited

U.S. PATENT DOCUMENTS

| | | | | |
|---|---|---|---|---|
| 4,056,969 A | * | 11/1977 | Barringer | 250/253 |
| 4,450,356 A | * | 5/1984 | Murray et al. | 250/339 |
| 4,489,239 A | * | 12/1984 | Grant et al. | 250/339 |
| 4,490,613 A | * | 12/1984 | Brame | 250/341 |
| 4,492,862 A | * | 1/1985 | Grynberg et al. | 250/255 |
| 4,616,134 A | * | 10/1986 | Pruett et al. | 250/255 |
| 4,853,543 A | * | 8/1989 | Ozdemir | 250/372 |
| 4,871,926 A | * | 10/1989 | Scott | 250/338.5 |
| 4,943,161 A | * | 7/1990 | Michaelis et al. | 356/437 |
| 5,157,257 A | * | 10/1992 | Geiger | 250/338.5 |
| 5,250,810 A | * | 10/1993 | Geiger | 250/338.5 |
| 6,269,108 B1 | * | 7/2001 | Tabirian et al. | 372/39 |

FOREIGN PATENT DOCUMENTS

GB 0489546 A2 * 11/1991 .......... G01N/21/35

* cited by examiner

Primary Examiner—Constantine Hannaher
Assistant Examiner—Otilia Gabor
(74) Attorney, Agent, or Firm—Edwin H. Crabtree; Ramon L. Pizarro; Donald W. Mangolis

(57) ABSTRACT

An oil and gas exploration system and method for land and airborne operations, the system and method used for locating subsurface hydrocarbon deposits based upon a remote detection of trace amounts of gases in the atmosphere. The detection of one or more target gases in the atmosphere is used to indicate a possible subsurface oil and gas deposit. By mapping a plurality of gas targets over a selected survey area, the survey area can be analyzed for measurable concentration anomalies. The anomalies are interpreted along with other exploration data to evaluate the value of an underground deposit. The system includes a differential absorption lidar (DIAL) system with a spectroscopic grade laser light and a light detector. The laser light is continuously tunable in a mid-infrared range, 2 to 5 micrometers, for choosing appropriate wavelengths to measure different gases and avoid absorption bands of interference gases. The laser light has sufficient optical energy to measure atmospheric concentrations of a gas over a path as long as a mile and greater. The detection of the gas is based on optical absorption measurements at specific wavelengths in the open atmosphere. Light that is detected using the light detector contains an absorption signature acquired as the light travels through the atmosphere from the laser source and back to the light detector. The absorption signature of each gas is processed and then analyzed to determine if a potential anomaly exists.

36 Claims, 3 Drawing Sheets

OIL AND GAS EXPLORATION SYSTEM AND METHOD FOR DETECTING TRACE AMOUNTS OF HYDROCARBON GASES IN THE ATMOSPHERE

The U.S. Department of Energy has certain rights in this present invention under DOE contract No. DE-FGO3-92ER81318 and The U.S. Air Force has certain rights in this present invention under AF contract No. F29601-94-C-0065.

BACKGROUND OF THE INVENTION (a) Field of the Invention

This invention relates to an oil and gas exploration system and method of detecting gases in the atmosphere and more particularly, but not by way of limitation, to detecting hydrocarbon gases using field-scale, differential absorption lidar (DIAL) sensing techniques operating in a mid-infrared, 2 to 5 micrometers, spectral range.

(b) Discussion of Prior Art

Gases, that are trapped or generated within the earth, can escape and travel through the earth to the earth's surface and then into the atmosphere. While in the earth, the gases come in contact with or are created by deposits of hydrocarbons and thereby acquire some signature of the deposit. The atmosphere can be monitored for gases that are associated with the deposits of hydrocarbons. The subject invention described herein addresses the measurement of gases associated with a potential oil and gas deposit. The gas concentrations are then mapped over a survey area and the maps are analyzed for concentration anomalies as described herein. The gas anomalies are interpreted along with other exploration data to evaluate the value of the underground deposit.

An association of gases detected in the atmosphere with a hydrocarbon deposit may be direct or indirect. An example of a direct association is the release of hydrocarbon gases to the atmosphere from subsurface oil and gas deposits. The association is direct in that the gas itself is emitted into the atmosphere, albeit with a potentially modified composition.

Methane is produced from the thermal or biological breakdown of coal. The gas detected (methane) is not the same as the natural resource (coal), so the term "indirect" is used to describe this association. The term indirect association does not imply that the scientific basis for the association is weak. The process of converting coal to methane is well characterized in the scientific literature. Also, coalbed methane is a new and expanding area of production for the natural gas industry.

In the discussion of the subject invention, the term "target gases" is used to indicate gases that are associated either directly or indirectly with deposits of hydrocarbons. The measured atmospheric concentrations of target gases form the basis of the new exploration tool as described herein. Target gases must have some uniqueness to their association with the hydrocarbon deposit. For example, methane is produced in a number of ways. It may occur in the atmosphere as a result of emission from a hydrocarbon deposit, emission from a coal deposit, emission from wetlands with active populations of methane producing bacteria, emission from a leaking natural gas pipeline, etc. Sources of methane other than the hydrocarbon deposit are said to be environmental interferences. Environmental interferences complicate the association between a target gas and the hydrocarbon deposit and will vary in magnitude and type with standard geological factors such as soil type, hydrology, subsurface structure and composition as well as atmospheric conditions, weather and land use.

A non-unique gas such a methane is a useful target gas for fossil fuels if combined with additional measurements to create a unique association. Examples of additional measurements are: concentrations of other gases such as ethane, propane, etc., isotopic composition of the methane, type of vegetation present, soil moisture, proximity of pollution sources and wind direction. Individual gases or gas combinations that have very unique associations with the hydrocarbon deposit provide the most valuable exploration signatures.

Laser absorption spectroscopy (LAS) is a sensitive means of quantifying molecular concentrations in a variety of situations not amenable to other techniques. A main advantage of LAS is that the measurements is done "in situ" which enables rapid measurements with good spatial resolution in harsh environments such as plasma, high vacuum and chemical reaction chambers. For an absorption experiment, the ratio of the transmitted beam intensity to the initial beam intensity, $I(\forall,x)/I_o(\forall,x=0)$, is related to an absorber concentration, n, by Beer's Law.

$$\frac{I(v, x)}{I_o(v, x = 0)} e^{-\sigma(v)nx}$$

The molecular cross-section at frequency, $\forall$, is denoted $\sigma(\forall)$ and the path length over which the laser travels by x. For any given signal to a noise ratio (SNR) for the measurement of $I/I_o$, the measurement sensitivity can be increased by increasing the path length. This patent application includes a differential absorption lidar (DIAL) which samples long paths through the atmosphere.

A wide range of instruments have been developed which successfully detect most trace gases in the atmosphere. These instruments can be loosely categorized into point techniques which sample air at a specific point in space and remote sensing systems such as the numerous satellite-based systems which provide large-scale measurements of gas concentrations. There are numerous types of gas sources which, because of their unique spatial and temporal properties, cannot be accurately characterized by these techniques. For example, an underground reservoir which might contain methane, carbon dioxide or gases from polluted ground waters, can leak intermittently from many points along a surface fracture. Monitoring emissions from such sources requires a system which can measure minute concentrations quickly and over long paths. Long path differential absorption lidars (DIALs) meet these requirements.

There are a number of prior art patents that describe oil and gas exploration systems that include means for detecting trace gases in the atmosphere. Some of these systems operate in the microwave or the ultraviolet wavelength region. These systems are unlike the subject invention which operates in the mid-infrared wavelength range.

The following patents are mentioned since the systems described therein operate in the mid-infrared wavelength region for detecting hydrocarbon gases. In U.S. Pat. No. 4,450,356 to Murray et al., a frequency-mixed $CO_2$ laser beam is used for remote detection of gases in the atmosphere. The laser beam system uses frequency doubling and frequency summing in crystals to produce wavelengths near 3 micrometers. This type of $CO_2$ laser system's wavelength is not continuously tunable.

In U.S. Pat. No. 4,489,239 to Grant et al., a portable remote laser sensor is described for detecting methane gas. The system requires the use of two lasers. The two lasers operate at two different wavelengths, each of which is fixed.

The detector must be kept at liquid nitrogen temperatures and does not operate at room temperatures. Further, the two lasers are not tunable and are used for detecting methane only. In U.S. Pat. No. 4,871,916 to Scott, a laser system, using glass lasers, is described for detecting explosive amounts, 40,000 parts per million (ppm), of methane only. In this system, the wavelength region is near 1.3 micrometers and the lasers are not tunable.

In U.S. Pat. Nos. 5,157,257 and 5,250,810 to Geiger, a mid-infrared light hydrocarbon DIAL lidar is described. The system uses six distinct coherent beams formed by six different lasers. The beams are combined into a single transmitted beam. While the six lasers are tunable, they include crystals which are easily damaged by high energy laser pulses. The complexity of this type of DIAL is not conducive to use in the field. Also, the spectral width is too broad to resolve the absorption bands of many key gases.

None of the above mentioned patents disclose or describe the unique features, structure, function and method steps of the subject oil and gas exploration system and method of detecting trace amounts of hydrocarbon gases in the field and in the mid-infrared region using a DIAL system with a single spectroscopic grade laser source.

SUMMARY OF THE INVENTION

In view of the foregoing, it is a primary object of the subject invention to provide a unique oil and gas exploration tool which is able to detect sub parts per million (ppm) amounts of hydrocarbon gases in the atmosphere.

Another object of the invention is the subject DIAL system can be used for mapping a plurality of target gases over a selected survey area. The maps are analyzed for concentration anomalies that indicate the presence of a potential hydrocarbon reservoir.

Yet another object of the DIAL system is its ability to achieve high energy laser pulses, in the mid-infrared wavelength range, 2 to 5 micrometers, with excellent spatial and spectral quality. The term "spectroscopic grade laser" used herein refers to lasers that produce light with a spectral width at least a factor of ten less than the spectral width of the target gas absorption bands used to make the DIAL measurements. Good spectral control enables the system to detect trace amounts of specific gases, such as ethane, methane and propane.

Still another object and key feature is the DIAL system is tunable for choosing appropriate wavelengths to measure different gases. Because the system is tunable, absorption bands of interference gases, such as water vapor and $CO_2$, can be avoided and the wavelengths can be chosen resulting in the most sensitive detection of a particular target gas.

A further object of the invention is the system allows trace gases to be accurately detected over one mile (two mile round trip) paths and greater and in a time span of under one minute.

Another object in the invention is the system is housed in a mobile trailer for transporting to various field locations. The system is operable and reliable for field applications and under harsh weather conditions. Also, the mid-infrared laser beam emitted is eye safe at all energy levels and at all wavelengths.

The system includes a differential absorption lidar (DIAL) system with a spectroscopic grade laser, a laser light and a light detector. The laser light is broadly tunable in the mid-infrared wavelength range, 2 to 5 micrometers, of the electromagnetic spectrum from which the appropriate wavelengths to measure different hydrocarbon gases and avoid absorption bands of interference gases can be chosen. The DIAL system with the laser light source is housed in a mobile platform for field operation. Also, the DIAL system can be used on an airborne platform for airborne survey applications. The laser light has sufficient optical energy to measure atmospheric concentrations of a selected gas over a path as long as a mile and greater. The detection of the target gas is based on optical absorption measurements at specific wavelengths in the open atmosphere. Light that is detected, using the light detector, contains an absorption signature acquired as the light travels through the atmosphere from the laser source and back to the light detector. The absorption signature of each target gas is processed and then analyzed to determine the gas concentration in the atmosphere. The target gas concentrations are mapped and analyzed to determine presence of concentration anomalies.

These and other objects of the present invention will become apparent to those familiar with the different types of hydrocarbon gas detection systems and methods when reviewing the following detailed description, showing novel construction, combination, and elements as herein described; and more particularly defined by the claims, it being understood that changes in the embodiments to the herein disclosed invention are meant to be included as coming within the scope of the claims, except insofar as they may be precluded by the prior art.

DESCRIPTION OF THE PREFERRED EMBODIMENTS

Figure 1:
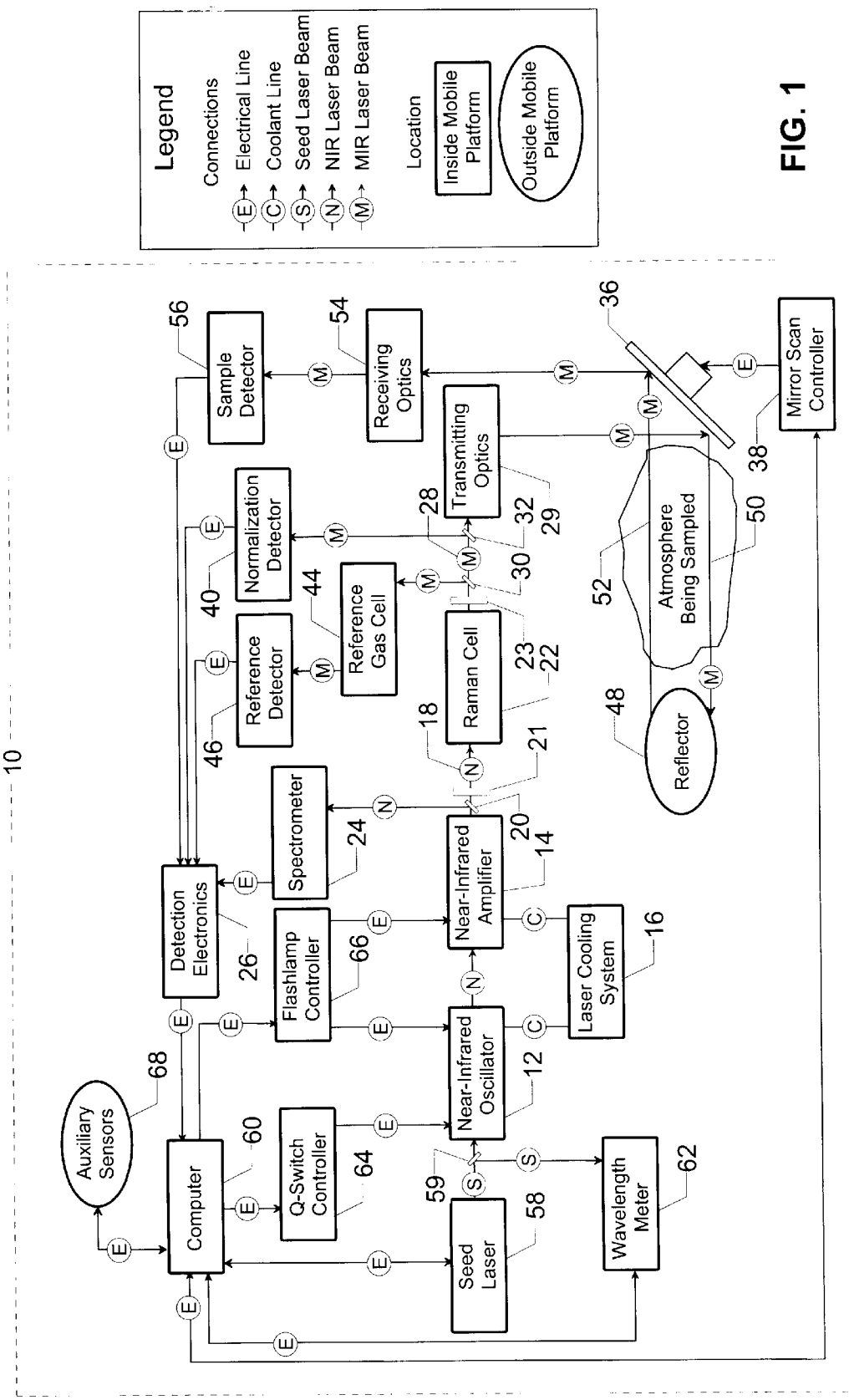
FIG. 1 is a block diagram of the components making up the subject DIAL system for detecting trace amounts of hydrocarbon gases.

The accompanying drawings illustrate complete preferred embodiments of the present invention according to the best modes presently devised for the practical application of the principles thereof, and in which:

In FIG. 1, a differential absorption lidar DIAL system operating in a 2–5 micrometer wavelength band is illustrated and having general reference numeral 10. The DIAL system 10 is based on a Raman-shifted, Cr:LiSAF laser. A similar DIAL system, but not described for use in detecting trace amounts of hydrocarbon gases for oil and gas exploration, is illustrated in U.S. Pat. No. 5,583,877 issued to MacPherson et al. and assigned to Ophir Corporation, Littleton, Colo. The subject matter found in this patent is incorporated herein by reference.

A brief description of Raman shifting follows as an aid in clearly describing various embodiments of the invention. The use of a Raman cell to shift the wavelength of light is well-described in the prior art. In basic terms of energy conservation, the process can be described as the energy of photons encountering gas in the Raman cell is shifted by an amount equal to the change in vibrational energy of the gas in the Raman cell. Expressed mathematically, $\Delta E photon = \Delta Evibgas$ where $\Delta E photon$ is the change in energy of the photon and Evibgas is the change in the vibrational energy of the gas in the Raman cell. This process also shifts the wavelength of the photons because the energy and the wavelength of a photon are related by the formula, $E=hc/\lambda$, where E designates the energy of the photon, h is Planck's constant, c is the speed of light and $\lambda$ is the wavelength of the photon. The energy of incident photons may be shifted to higher energy (anti-Stokes Shift) or to lower energy (Stokes shift) and multiple shifts can occur. Light that undergoes a single Stokes shift is referred to as S1 light and light that under two Stokes shifts is referred to as S2. Similarly, light that undergoes a single anti-Stokes shift is referred to as AS1 and two anti-Stokes shifts results in AS2 light. The incident light is designated S0. In a typical operation, S0 light is incident on the Raman cell and a filter is used after the Raman cell to eliminate AS2, AS1, S0 and S1 light components leaving only S2 to comprise the mid-infrared light.

The DIAL system 10 is unique in that it achieves continuously wavelength-tunable, high energy laser pulses with excellent spatial and spectral quality. The system allows individual gases to be accurately quantified over one mile (two mile round trip) paths and greater in under one minute. While not shown in the drawings, the system is housed in a mobile trailer allowing it to be used to survey different types of exploration sites. Also, the system 10 has been developed to operate reliably even under harsh weather conditions.

The system 10 broadly includes the following. A laser oscillator 12 optically connected to a laser amplifier 14. A recirculating water chiller 16, using buffered distilled water, is connected to both the oscillator 12 and amplifier 14. The chiller 16 is used for cooling Cr:LiSAF laser rods in the oscillator 12 and amplifier 14.

A 750–950 nm pulsed near infrared laser light 18 is directed outwardly through a first partial reflective mirror 20 and a polarization filter 21 to a hydrogen filled Raman cell 22. A portion of the light 18 is reflected to a spectrometer 24, which in turn is electrically connected to detection electronics 26. From the Raman cell 22, the light pulses pass through a wavelength filter 23 to remove residual near infrared, anti-Stokes and first Stokes components. From the wavelength filter 23, 2–5 micrometer pulsed mid-infrared light 28 is directed through a second partial reflective mirror 30, through a third partial reflective mirror 32 and through transmitting optics 29 onto a transmission mirror 36. The transmission mirror 36 is mounted in a two-axis rotational stage to allow spatial scanning of the laser light 28.

The transmission mirror 36 is operated under a mirror scan control 38. The second partial reflector 30 directs a portion of the light 28 to a reference gas cell 44 and onto a reference detector 46. The reference detector 46 is electrically connected to the detection electronics 26 for monitoring transmission through the reference gas cell 44.

The third partial reflector 32 directs a portion of the light 28 to a normalization detector 40, which in turn is electrically connected to detection electronics 26 for measuring the laser pulse energy.

From the transmission mirror 36, the 2–5 micrometer light 28 is transmitted to a retroreflector 48 over a transmission path through the atmosphere, as indicated by arrow 50. Redirected light 52, also shown as an arrow, is reflected back to the transmission mirror 36 to receiving optics 54 and received by a sample detector 56. The sample detector 56 is electrically connected to the detection electronics 26.

The DIAL system 10 also includes a diode seed laser 58 optically connected to the laser oscillator 12 and also electrically connected to, a computer 60 and optically connected to a wavelength meter 62. The wavelength meter 62 is electrically connected to the computer 60. A Q switch controller 64 and a flashlamp controller 66 are both electrically connected between the computer 60 and the laser oscillator 12. The flashlamp controller 66 is also electrically connected to the laser amplifier 14.

The laser amplifier 14 is a Cr:LiSAF, single pass amplifier. Together the oscillator 12 and amplifier 14 generate near infrared Q-switched pulses with pulse energies of 40 millijoules and pulse widths of 80 nanoseconds at a pulse repetition frequency of 2 Hz. Also, the pulses are in the 780 to 980 nanoseconds spectral band.

The configuration of the diode seed laser 58, the laser oscillator 12, the laser amplifier 14 and the Raman cell 22 are chosen in order to improve the reliability of the laser light source under harsh field conditions. For example, the pulses extracted from the oscillator 12 are amplified by a factor of two in a single pass through the amplifier 14. For equivalent output pulse energies, this optical configuration reduces the thermal load on the Cr:LiSAF crystal rods incorporated into the oscillator 12 and thereby reduces the energy density in the oscillator cavity relative to a similar configuration without an amplifier stage. Though not shown in FIG. 1, the coupling between the diode seed laser 58 and the laser oscillator 12 can be actively controlled using standard techniques. Active control increases the seeding efficiency, but adds complexity to the system.

The Cr:LiSAF is a uniaxial crystal, which rotates the polarization of light as the light passes through the crystal according to the standard principals governing polarization rotation in birefringent crystals. The magnitude of the birefringent effect is very sensitive to the temperature of the Cr:LiSAF crystals. The temperature of the cooling water circulated by the chiller 16 is controlled with fluctuations in a range of plus or minus 1 degree C. Small misalignments of the optical axis of the Cr:LiSAF amplifier rod in the amplifier 14 result in large temperature driven polarization changes in the pulses that pass through the amplifier. Polarization effects throughout the remainder of the optical path are overcome with the use of the polarization filter 21 between the amplifier 14 and the Raman cell 22.

Referring now to the Raman cell 22, stimulated Raman scattering of the light 18 in hydrogen is used to shift the near infrared Cr:LiSAF laser pulses into the mid-infrared light 28, where many of the hydrocarbon gases have strong absorption bands. Stokes shifts of approximately 4155 wavenumbers arise from the Q(1) vibrational Raman transition in the hydrogen. The hydrogen is held at room temperature and at a pressure of 10 atmospheres. Second Stokes conversion of the Cr:LiSAF pulses to the mid-infrared is enhanced by use of a multiple pass design for the Raman cell 22.

The stimulated Raman scattering has several important advantages over other nonlinear wavelength shifting techniques. The subject technique is extremely efficient with up to an 80 percent quantum efficiency in conversion of the near infrared light 18 to the mid-infrared light 28 when the laser energy is well above the stimulated Raman scattering threshold for shifting the wavelength of the light. This technique is inherently "phase-matched". Also, the mid-infrared light 28, can be tuned anywhere over a 2.2 to 5.2 micrometer wavelength band simply by tuning the near-infrared laser light 18 from 780 to 980 nanometers. This key feature is in contrast to other prior art nonlinear methods for producing mid-infrared light, as mentioned above, where optical crystals need to be rotated or heated in a controlled fashion to achieve tuning. Further, another advantage of the use of the Raman cell 22 is optical damage does not occur to the nonlinear medium which is hydrogen.

Referring to the transmission of the 2–5 micrometer light 28 to the retroreflector 48, anti-Stokes (AS1 and AS2), first Stokes (S1) and residual near infrared components (S0) are removed from the second Stokes output of the Raman cell 22 with the wavelength filter 23. The wavelength filter 23 is a 3.3 micrometer, anti-reflection coated germanium filter. This ensures that only an eyesafe laser is transmitted into the atmosphere. The beam of the light 28 is expanded to a 4 inch diameter, collimated and directed through the atmosphere to the retroreflector 48 as shown in FIG. 1. The retroreflector 48 is a 40 centimeter diameter array of corner-cube reflectors. While the retroreflector 48 is mentioned and is ideal for this type of system, it should be kept in mind various naturally occurring and man made physical objects can be used for reflecting the light beam. The redirected light 52 from the retroreflector 48 is collected by the receiving optics 54. The receiving optics 54, for example, can include a collection telescope such as a 12.5 inch custom Newtonian telescope. As indicated by arrow 50, the optical path may be up to or greater than one mile with the system 10 having sufficient pulse energy to extend well beyond this range.

The three detectors 40, 46 and 56 are used in the system 10 to measure the laser pulse energies at various points in the system 10. The detectors are uncoated pyroelectric crystals with an active diameter of 2 millimeters and include.integrated battery powered pre-amplifiers. Other types of detectors may also be used.

The computer 60 is used to the control the system 10, to perform health checks to verify proper functionality, log the numerous data channels, process the data to give a real time or time-averaged gas concentration value and display data. The software used by the computer 60 was developed for controlling various subsystems and peripheral equipment interfaced with the computer. Serial ports of the computer are used to collect auxiliary data such as wind speed and direction, temperature, barometric pressure and humidity from a weather station and Global Positioning System (GPS) coordinates of the mobile unit housing the system 10 and the retroreflector 48. Also, the computer 60 receives inputs from the detectors 40 and 46 and in addition to the signal from the main redirected light 52 which are automatically logged for each laser shot to monitor the quality of the data and verify that the system is operating properly.

A small portion of the mid-infrared pulse light 28 is detected for outgoing pulse normalization. Another small portion of the mid-infrared light 28 is sent through the reference gas cell 44. The cell 44 is filled with a known composition of gas and provides a turbulence-free differential absorption measurement which can be used to verify that the outgoing light 28 has a proper wavelength and spectral width.

Coarse, near infrared wavelength measurements are calculated from the output of a diode array detector mounted on the output port of the spectrometer 24. Properly seeded pulses are much narrower (spectrally) than the spectrometer resolution while unseeded pulses are not. This feature provides feedback to an operator during the initial optimization of the seeding alignment.

Also shown in FIG. 1 are auxiliary sensors 68 connected to the computer 60. The auxiliary sensors 68 include a weather station and GPS receivers. The temperature, humidity, barometric pressure, wind speed and wind direction from the weather station are recorded with each lidar pulse of the system 10. The latitude and longitude of the mobile trailer and the retroreflector 48 are determined for each atmospheric path. The communication with the GPS receiver that is located at the retroreflector 48 is achieved with a battery powered radio frequency modem. Differential GPS readings with a standard deviation of less than plus or minus 2 meters at distances to 1500 meters are used to accurately measure the path length in order to extract calibrated wavelength concentration measurements that are described herein.

While not shown in FIG. 1, a first alternate embodiment of the DIAL system 10 is now described and referred to as a "seeded Raman" embodiment. In the seeded Raman embodiment, the seed laser 58 operates at mid-infrared wavelengths and is optically coupled directly to the Raman cell 22 rather than connected to the near-infrared oscillator 12. There are several benefits of the seeded Raman embodiment. The first benefit is that lower pulse energy densities are required to achieve equivalent Raman shifting efficiency. Lower optical energy densities lead to less power consumption, less chance for optical damage, and thereby increased lifetime of the system. The second benefit is that the wavelength meter 62 in the DIAL system 10 can be replaced with a gas cell, similar to the reference gas cell channel described in the preferred embodiment and associated detector and detection electronics. Gas cells are simple, rugged devices with no moving parts and require no periodic recalibration. Finally, the variation in pulse energy for light 18 produced by the near-infrared oscillator 12 and the amplifier 14 is reduced in the absence of seeding by the seed laser 58.

A second alternate embodiment of the DIAL system 10 is now described and called a "double pulse" embodiment. The double pulse embodiment takes advantage of two laser pulses generated from the Cr:LiSAF laser rods in the near-infrared oscillator 12. The two laser pulses are called a "double pulse" because the two pulses can be generated with less than a millisecond delay between the two pulses. The pulse pairs can be generated at a 2 Hz rate already described for the DIAL system 10. Further, one pulse of the pulse pair can be emitted with a wavelength corresponding to an "on line", absorbed, wavelength and the other pulse of the pulse pair can be emitted with.a wavelength corresponding to an "off line", not absorbed, wavelength in order to perform a differential absorption measurement.

Figure 5:
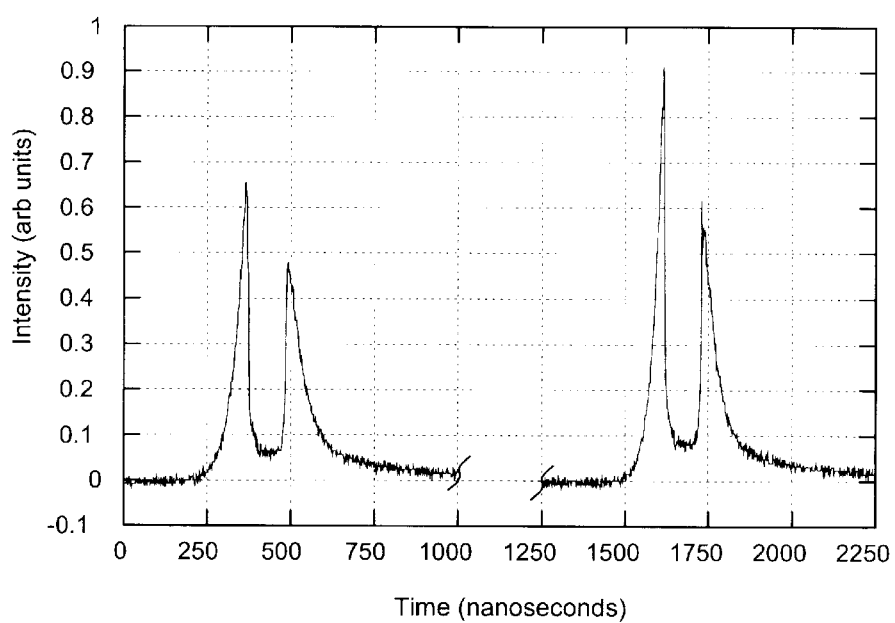
FIG. 5 illustrates data showing that the system described herein demonstrates the generation of two mid-infrared laser pulses separated by less than 1 millisecond.

In FIG. 5, data is shown to demonstrate the ability of the subject invention to support the double-pulse embodiment. The plot shown in FIG. 5 shows the intensity of the S0(pump) beam as a function of time. Without Raman shifting, the pulses are expected to exhibit a Gaussian shape. The high intensity portion of each pulse is missing because at these intensities a significant portion of the pump beam is shifted from the near-infrared (S0) to the mid-infrared (S2). The two pulses occur 43 microseconds apart and both show conversion to S2.

The benefit of using pulse pairs for the differential absorption measurement is that the atmosphere appears frozen on this time scale, because atmospheric motions that affect open path optical measurements occur on longer time scales. Therefore, the on line and off line measurements occur essentially simultaneously, which is the preferred technique for DIAL measurements. Further, the double pulse embodiment is possible only if the Raman cell 22 is capable of shifting both the pulses of a pulse pair from the near infrared to the mid-infrared spectral range. A second benefit is that the data acquisition rate is essentially doubled even though the main repetition rate of the system remains at 2 Hz. In the preferred embodiment of the DIAL system 10 described above, the reference detector 46, the normalization detector 40 and the sample detector 56 were all described more specifically to be pyroelectric detectors. Obviously to those skilled in the art, the relatively inexpensive pyroelectric detectors have to be replaced with higher speed detectors in order to detect the individual pulses of each pulse pair.

A third alternate embodiment of the DIAL system 10 is now described and called a "combined seeded Raman and double pulse" embodiment. This combined embodiment provides the benefits and advantages of the seeded Raman embodiment and the double pulse embodiment discussed above.

A fourth alternate embodiment of the DIAL system 10 is now described and called a "multiple wavelength" embodiment. The multiple wavelength embodiment is an alternative to the double-pulse embodiment. A common thread for the embodiments described heretofore is that each pulse produced by a given embodiment of the DIAL system 10 contains light with a single wavelength and is denoted as the mid-infrared light 28. Accordingly, differential absorption measurements are made by scanning the wavelength of the mid-infrared light 28. In the multiple wavelength embodiment, the filter 23 is designed to transmit S2 light and one or more of the AS2, AS1, S0 and S1 components produced or transmitted by the Raman cell 22. Light, comprised of the multiple wavelengths is transmitted through the atmosphere, reflected and received in the same manner as a single wavelength mid-infrared light 28.

The functions of the reference detector 46, the normalization detector 40 and the sample detector 56 are fulfilled with wavelength selective detection in order to carry out differential optical absorption measurements with a single laser pulse. Wavelength selective detection can be achieved with the use of composite detectors that quantify the amount of light received at different wavelengths or through the use of wavelength dependent beam splitters and additional non-wavelength specific detectors.

The benefit of the multiple wavelength embodiment is that the multiple wavelengths are transmitted, reflected and received simultaneously. Therefore, atmospheric turbulence has little impact. A second benefit is that the non-mid-infrared beams can be used to collect other data about the atmosphere. The other data includes windspeed, aerosol concentrations, aerosol composition and water vapor concentration. Appropriate precautions must be taken to ensure eye safety when using this embodiment, since the multiple wavelength laser beam is not necessarily eye safe when the wavelength filter 23 is removed.

Figure 2:
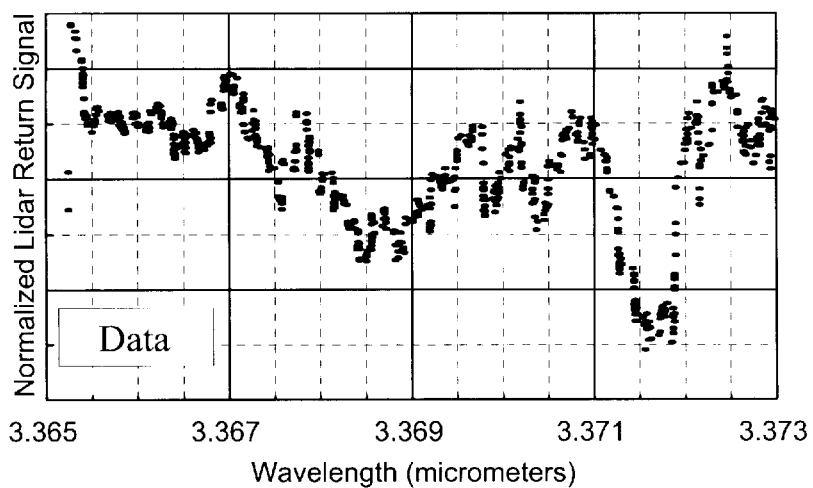
FIG. 2 illustrates a normalized lidar signal vs. wavenumber, near 3.37 micrometers, for ambient urban air over a 480 meter path. This graph shows data from the subject DIAL system indicating the presence of water vapor and methane in the ambient atmosphere.

In FIG. 2, a normalized lidar signal vs. wavenumber spectrum, near 3.37 micrometers, is illustrated for ambient urban air over an open path. The open path is 480 meters and data is for a 0.008 nanometer scan. The data show optical absorption features for methane and water with a total of seven features in this spectral region. The laser source in the system 10 is sufficiently narrow to resolve two water absorption features that are separated by just 0.0005 nanometers. The near infrared tuning range of the injected seeded laser oscillator 12 and amplifier 14 is greater than 0.5 nanometers without any operator intervention.

Figure 3:
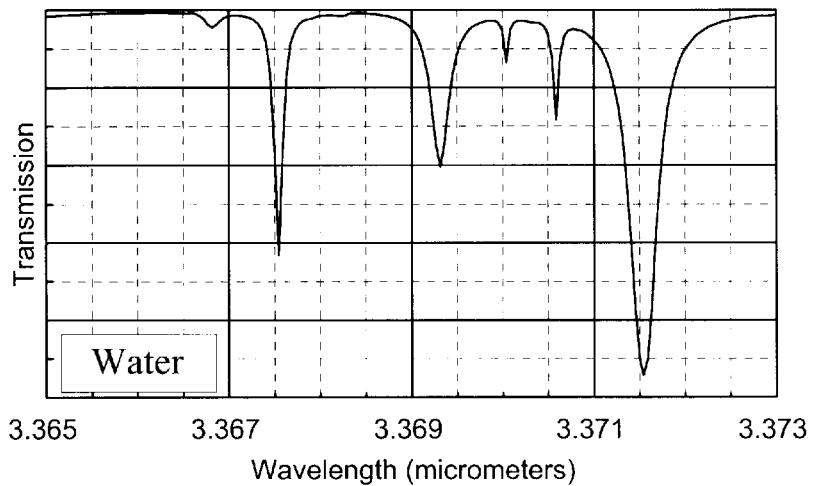
FIG. 3 illustrates a theoretical absorption methane spectrum in the 3.365 to 3.373 micrometer range.

In FIG. 3, a theoretical absorption methane spectrum based upon the 1996 HITRAN molecular database is illustrated. This spectrum is in a 3.365 to 3.373 micrometer range.

Figure 4:
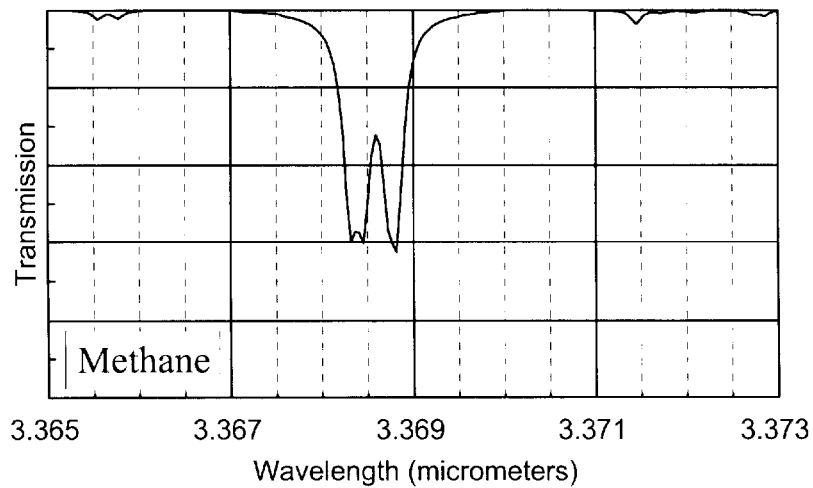
FIG. 4 illustrates a theoretical absorption water vapor spectrum in the 3.365 to 3.373 micrometer range.

In FIG. 4, a theoretical absorption water vapor spectrum based upon the 1996 HITRAN molecular absorption database is illustrated. This spectrum is also in the 3.365 to 3.373 micrometer range.

While the invention has been shown, described and illustrated in detail with reference to the preferred embodiments and modifications thereof, it should be understood by those skilled in the art that equivalent changes in form and detail may be made therein without departing from the true spirit and scope of the invention as claimed, except as precluded by the prior art.

The embodiments of the invention for which an exclusive privilege and property right is claimed are defined as follows:

1. An oil and gas exploration system for land and airborne operations, the system used for locating subsurface hydrocarbon deposits based upon a remote detection of a selected target gas in the atmosphere, the system comprising;

a diode seed laser connected to a laser oscillator;

an amplifier connected to said laser oscillator, whereby said seed laser, said laser oscillator and said amplifier provide a near-infrared laser light source and generate a near-infrared light;

a hydrogen filled Raman cell connected to said amplifier, said Raman cell for converting said near infrared light to a mid-infrared light, said mid-infrared light in a 2 to 5 micrometer wavelength band range, said mid-infrared light having sufficient optical energy to measure atmospheric gas concentrations over a selected path in the atmosphere, whereby said mid-infrared light has a spectral width sufficiently less than a spectral width of the selected target gas for spectral control in detecting trace amounts of the selected target gas in the atmosphere;

means for continuously tuning said mid-infrared light by tuning said near-infrared light;

a light detector adapted for detecting an absorption signature of the selected target gas in said tuned mid-infrared light, said absorption signature acquired as said tuned mid-infrared light travels through the atmosphere from said Raman cell and back to said light detector; and means for processing said absorption signature to determine a presence or an absence of the selected target gas in the atmosphere.

2. The system as described in claim 1 wherein the selected path in the atmosphere is as long as a mile and greater.

3. The system as described in claim 1 wherein said tuned mid-infrared light is returned back to said detector using a reflective object.

4. An oil and gas exploration system for land and airborne operations, the system used for locating subsurface hydrocarbon deposits based upon a remote detection of a selected target gas in the atmosphere, the system comprising;

a diode seed laser connected to a laser oscillator;

an amplifier connected to said laser oscillator, whereby said seed laser, said laser oscillator and said amplifier provide a near-infrared laser light source and generate a near-infrared light;

a hydrogen filled Raman cell connected to said amplifier, said Raman cell for converting said near-infrared light to a mid-infrared light, said mid-infrared light in a 2 to 5 micrometer wavelength band range, said mid-infrared light having sufficient optical energy to measure atmospheric gas concentrations over a selected path in the atmosphere, whereby said mid-infrared light has a spectral width sufficiently less than a spectral width of the selected target gas for spectral control in detecting trace amounts of the selected target gas in the atmosphere;

means for continuously tuning said mid-infrared light by tuning said near-infrared light;

a light detector adapted for detecting an absorption signature of the selected target gas in said tuned mid-infrared light, said absorption signature acquired as the tuned mid-infrared light travels through the atmosphere from said Raman cell and back to said light detector; and means for reflecting said mid-infrared light back to said light decor; and computer means for processing data of said absorption signature to determine a presence or an absence of the selected target gas in the atmosphere.

5. The system as described in claim 4 wherein said laser oscillator and said amplifier include Cr:LiSAF crystal rods mounted therein.

6. The system as described in claim 5 further including flashlamps and flashlamp controllers for pumping said Cr:LiSAF crystal rods in said laser oscillator and said laser oscillator.

7. The system as described in claim 4 wherein said Raman cell is used for shifting two near-infrared Cr:LiSAF laser pulses from said laser oscillator, said Raman cell generating two mid-infrared pulses with less than a millisecond delay.

8. The system as described in claim 4 wherein said means for continuously tuning said mid-infrared light tunes said near-infrared light in a range of 780 to 980 nanometers.

9. The system as described in claim 4 wherein said means for reflecting said mid-infrared light back to said light detector is a retroreflector.

10. The system as described in claim 9 wherein said mid-infrared light reflected back by said retroreflector is collected by a receiving optic, said receiving optics connected to detection electronics, said detection electronic connected to said computer means.

11. An oil and gas exploration system for land and airborne operations, the system used for locating subsurface hydrocarbon deposits based upon a remote detection of a selected target gas in the atmosphere, the system comprising;

a diode seed laser connected to a laser oscillator;

an amplifier connected to said laser oscillator, whereby said seed laser, said laser oscillator and said amplifier provide a near-infrared laser light source and generate a near-infrared light in a 780 to 980 nanometer wavelength band, a hydrogen filled Raman cell connected to said amplifier, said Raman cell for converting said near infrared light to a mid-infrared light, said mid-infrared light in a 2 to 5 micrometer wavelength band range, said mid-infrared light having sufficient optical energy to measure atmospheric gas concentrations over a selected path in the atmosphere, whereby said mid-infrared light has a spectral width sufficiently less than a spectral width of the selected target gas for spectral control in detecting trace amounts of the selected target gas in the atmosphere;

means for continuously tuning said mid-infrared light by tuning said near-infrared light;

a light detector adapted for detecting an absorption signature of the selected target gas in said tuned mid-infrared light, said absorption signature acquired as said tuned mid-infrared light travels through the atmosphere from said Raman cell and back to said light detector; and computer means for processing data of said absorption signature to determine a presence or absence of the selected target gas in the atmosphere.

12. The system as described in claim 11 wherein said laser oscillator and said amplifier include Cr:LiSAF crystal rods mounted therein.

13. The system as described in claim 12 further including flashlamps and flashlamp controllers for pumping said Cr:LiSAF crystal rods in said laser oscillator and said laser oscillator.

14. The system as described in claim 11 wherein said Raman cell is used for shifting two near-infrared Cr:LiSAF laser pulses from said laser oscillator, said Raman cell generating two mid-infrared pulses with less than a millisecond delay.

15. The system as described in claim 11 wherein said laser oscillator and said laser amplifier generate near-infrared Q-switched pulse energies of 40 millijoules.

16. The system as described in claim 11 wherein said laser oscillator and said amplifier generate pulse widths of 80 nanoseconds.

17. The system as described in claim 11 further including a laser cooling system, said laser cooling system connected to said laser oscillator and said laser amplifier.

18. The system as described in claim 11 further including a wavelength filter, said wavelength filter connected to said Raman cell, said filter used for removing near-infrared, anti-Stokes, a first Stokes components from said mid-infrared light.

19. The system as described in claim 11 wherein said computer means is connected to a weather station for obtaining auxiliary data including wind speed and direction, temperature, barometric pressure and humidity.

20. The system as described in claim 11 wherein said means for reflecting is a retroreflector and said computer means is connected to GPS receivers, said GPS receivers used for obtaining auxiliary data including coordinates of a mobile unit for housing the exploration system and said retroreflector.

21. An oil and gas exploration system for land and airborne operations, the system used for locating subsurface hydrocarbon deposits based upon a remote detection of a selected target gas in the atmosphere, the system comprising;

a diode seed laser connected to a laser oscillator;

an amplifier connected to said laser oscillator, whereby said seed laser, said laser oscillator and said amplifier provide a near-infrared laser light source and generate a near-infrared light, the near-infrared light having a first wavelength at S2 and a second wavelength at AS2, AS1, S$\phi$ and S1, said first and second wavelengths adapted for performing differential optical absorption measurements of the selected target gas in the atmosphere;

a hydrogen filled Raman cell connected to said amplifier, said Raman cell for converting said near infrared light to a mid-infrared light, said mid-infrared light in a 2 to 5 micrometer wavelength band range, said mid-infrared light having sufficient optical energy to measure atmospheric gas concentrations over a selected path in the atmosphere, whereby said mid-infrared light has a spectral width sufficiently less than a spectral width of the selected target gas for spectral control in detecting trace amounts of the selected target gas in the atmosphere;

means for continuously tuning said mid-infrared light by tuning said near-infrared light;

a light detector adapted for detecting an absorption signature of the selected target gas in said tuned mid-infrared light, said absorption signature acquired as said tuned mid-infrared light travels through the atmosphere from said Raman cell and back to said light detector; and means for processing said absorption signature to determine a presence or an absence of the selected target gas in the atmosphere.

22. A method for locating subsurface hydrocarbon deposits based upon a remote detection of trace amounts of a selected target gas in the atmosphere, the method using a spectroscopic grade laser light source, the steps comprising:

generating a near-infrared light using a combination of a diode seed laser, a laser oscillator and an amplifier, receiving the near-infrared light in a Raman cell, the Raman cell converting the near-infrared light to a mid-infrared light in a 2 to 5 micrometer wavelength band range and emitting the mid-infrared light into the atmosphere, the mid-infrared light having sufficient optical energy to measure atmospheric gas concentrations over a selected path in the atmosphere;

continuously tuning the mid-infrared light by tuning the near-infrared light;

detecting an absorption signature of the selected target gas in the tuned mid-infrared light using a light detector, the absorption signature acquired as the tuned mid-infrared light travels through the atmosphere from the Raman cell and back to the light detector; and processing the absorption signature using data processing equipment to determine a presence or an absence of the selected target gas in the atmosphere.

23. The method as described in claim 22 wherein the selected path in the atmosphere is as long as a mile and greater.

24. The method as described in claim 22 wherein the laser oscillator and amplifier include Cr:LiSAF crystal rods mounted therein.

25. The method as described in claim 24 wherein the Raman cell converts near-infrared Cr:LiSAF laser pulses to the mid-infrared light in the 2 to 5 micrometer wavelength band range and emitting.

26. The method as described in claim 24 further including the step of pumping the Cr:LiSAF crystal rods in the laser oscillator and the amplifier using flashlamps and flashlamp controllers.

27. The method as described in claim 24 wherein the Raman cell converts two near-infrared Cr:LiSAF laser pulses to the mid-infrared light wit two pulses with less than a millisecond delay.

28. The method as described in claim 22 wherein the step of tuning the mid-infrared light includes tuning the near-infrared light in a range of 780 to 980 nanometers.

29. The method as described in claim 22 further including the step of reflecting back the mid-infrared light to the light detector.

30. The method as described in claim 29 wherein the step of reflecting back the mid-infrared light includes using a retroreflector for reflecting back the mid-infrared light.

31. The method as described in claim 30 further including the step of connecting the data processing equipment to GPS receivers, the GPS receivers used for obtaining auxiliary data including coordinates of a mobile unit, the mobile unit housing the exploration system and retroreflector used for reflecting the mid-infrared light.

32. The method as described in claim 29 further including the step of, after reflecting back the mid-infrared light to the light detector, collecting the reflected light using receiving optics connected to detection electronics, the detection electronics connected to the data processing equipment.

33. The method as described in claim 22 further including the step of cooling the near-infrared light received by the Raman cell using a laser cooling system.

34. The method as described in claim 22 further including the step of filtering the mid-infrared light using a wavelength filter connected to the Raman cell, the wavelength filter used for filtering near-infrared light, anti-stokes and first stokes components from the laser light.

35. The method as described in claim 22 further including the step of connecting the data processing equipment to a weather station for obtaining auxiliary data including wind speed and direction, temperature, barometric pressure and humidity.

36. A method for locating subsurface hydrocarbon deposits based upon a remote detection of trace amounts of a selected target gas in the atmosphere, the method using a spectroscopic grade laser light source, the steps comprising:

generating a near-infrared light having a first wavelength of S2 and a second wavelength at AS2, AS1, S$\phi$ and S1 for performing differential optical absorption measurements of the selected target gas and using a combination of a diode see laser, a laser oscillator and an amplifier, receiving the near-infrared light in a cell, converting the near-infrared light to a mid-infrared light in a 2 to 5 micrometer wavelength band range and emitting the mid-infrared light into the atmosphere, the mid-infrared light having sufficient optical energy to measure atmospheric gas concentrations over a selected path in the atmosphere;

continuously tuning the mid-infrared light by tuning the first and second wavelengths of the near-infrared light;

detecting an absorption signature of the selected target gas in the tuned mid-infrared light, the absorption signature acquired as the tuned mid-infrared light travels through the atmosphere from the Raman cell and back to the light detector; and processing the absorption signature using data processing equipment to determine a presence or an absence of he selected target gas in the atmosphere.

* * * * *